United States Patent
Liff et al.

(10) Patent No.: US 11,223,524 B2
(45) Date of Patent: Jan. 11, 2022

(54) PACKAGE INTEGRATED SECURITY FEATURES

(71) Applicant: Intel Corporation, Santa Clara, CA (US)

(72) Inventors: Shawna M. Liff, Scottsdale, AZ (US); Adel A. Elsherbini, Chandler, AZ (US); Sasha N. Oster, Chandler, AZ (US); Feras Eid, Chandler, AZ (US); Georgios C. Dogiamis, Chandler, AZ (US); Thomas L. Sounart, Scottsdale, AZ (US); Johanna M. Swan, Scottsdale, AZ (US)

(73) Assignee: Intel Corporation, Santa Clara, CA (US)

( * ) Notice: Subject to any disclaimer, the term of this patent is extended or adjusted under 35 U.S.C. 154(b) by 661 days.

(21) Appl. No.: 16/152,280

(22) Filed: Oct. 4, 2018

(65) Prior Publication Data
US 2019/0036774 A1    Jan. 31, 2019

Related U.S. Application Data

(62) Division of application No. 15/283,129, filed on Sep. 30, 2016, now Pat. No. 10,116,504.

(51) Int. Cl.
*H01L 41/04* (2006.01)
*H04L 12/24* (2006.01)
(Continued)

(52) U.S. Cl.
CPC ...... *H04L 41/0816* (2013.01); *A61B 5/02055* (2013.01); *A61B 5/7282* (2013.01);
(Continued)

(58) Field of Classification Search
CPC ............ H04L 41/0816; A61B 5/02055; A61B 5/7282; A61B 5/7285; A61B 5/08;
(Continued)

(56) References Cited

U.S. PATENT DOCUMENTS

| 4,868,448 A | 9/1989 | Kornrumpf |
| 6,035,366 A | 3/2000 | Teich |

(Continued)

FOREIGN PATENT DOCUMENTS

JP    2014-175301    9/2014

OTHER PUBLICATIONS

T. Le, G. Salles-Loustau, L. Najafizadeh, M. Javanmard and S. Zonouz, "Secure Point-of-Care Medical Diagnostics via Trusted Sensing and Cyto-Coded Passwords," 2016 46th Annual IEEE/IFIP International Conference on Dependable Systems and Networks (DSN), 2016, pp. 583-594, doi: 10.1109/DSN.2016.59. (Year: 2016).*

(Continued)

*Primary Examiner* — J. San Martin
(74) *Attorney, Agent, or Firm* — Schwabe, Williamson & Wyatt, P.C.

(57) ABSTRACT

Embodiments of the invention include a physiological sensor system. According to an embodiment the sensor system may include a package substrate, a plurality of sensors formed on the substrate, a second electrical component, and an encryption bank formed along a data transmission path between the plurality of sensors and the second electrical component. In an embodiment the encryption bank may include a plurality of portions that each have one or more switches integrated into the package substrate. In an embodiment each sensor transmits data to the second electrical component along different portions of the encryption bank. In some embodiments, the switches may be piezoelectrically actuated. In other embodiments the switches
(Continued)

may be actuated by thermal expansion. Additional embodiments may include tri- or bi-stable mechanical switches.

12 Claims, 9 Drawing Sheets

(51) Int. Cl.

| | | |
|---|---|---|
| *H01H 57/00* | (2006.01) | |
| *H01L 41/047* | (2006.01) | |
| *H01L 41/187* | (2006.01) | |
| *A61B 5/0205* | (2006.01) | |
| *A61B 5/00* | (2006.01) | |
| *H01L 41/09* | (2006.01) | |
| *A61B 5/024* | (2006.01) | |
| *A61B 5/021* | (2006.01) | |
| *A61B 5/08* | (2006.01) | |
| *A61B 5/145* | (2006.01) | |
| *H01H 37/00* | (2006.01) | |

(52) U.S. Cl.
CPC ........... *A61B 5/7285* (2013.01); *H01H 57/00* (2013.01); *H01L 41/0471* (2013.01); *H01L 41/094* (2013.01); *H01L 41/187* (2013.01); *H01L 41/1873* (2013.01); *H01L 41/1876* (2013.01); *H04L 41/0886* (2013.01); *A61B 5/021* (2013.01); *A61B 5/02405* (2013.01); *A61B 5/08* (2013.01); *A61B 5/145* (2013.01); *A61B 5/4266* (2013.01); *A61B 5/4824* (2013.01); *A61B 2560/0462* (2013.01); *H01H 2037/008* (2013.01); *H01H 2057/006* (2013.01)

(58) Field of Classification Search
CPC ..... A61B 5/145; A61B 5/4266; A61B 5/4824; H01H 57/00; H01H 2037/008; H01L 41/0471; H01L 41/094; H01L 41/187; H01L 41/1873; H01L 41/1876
See application file for complete search history.

(56) References Cited

U.S. PATENT DOCUMENTS

| | | | |
|---|---|---|---|
| 6,587,612 | B1 | 7/2003 | Mithchell |
| 7,774,852 | B2* | 8/2010 | Yokota .................. H04L 9/083 726/27 |
| 8,736,145 | B2* | 5/2014 | Liu ........................ B81B 3/0072 310/331 |
| 8,860,284 | B1 | 10/2014 | Fahimi |
| 9,028,407 | B1* | 5/2015 | Bennett-Guerrero ........................ A61B 5/4094 600/301 |
| 9,130,835 | B1 | 9/2015 | White |
| 2003/0008286 | A1 | 1/2003 | Zou |
| 2003/0167391 | A1 | 9/2003 | Al-Ali |
| 2005/0127792 | A1 | 6/2005 | Mehta |
| 2008/0287748 | A1 | 11/2008 | Sapounas et al. |
| 2009/0230250 | A1 | 9/2009 | Wehner |
| 2011/0168378 | A1 | 7/2011 | Hsu |
| 2015/0171768 | A1 | 6/2015 | Perreault |
| 2016/0188897 | A1 | 6/2016 | Zatko et al. |

OTHER PUBLICATIONS

International Search Report and Written Opinion from International Application No. PCT/US2017/049217, dated Dec. 7, 2017, 14 pages.

\* cited by examiner

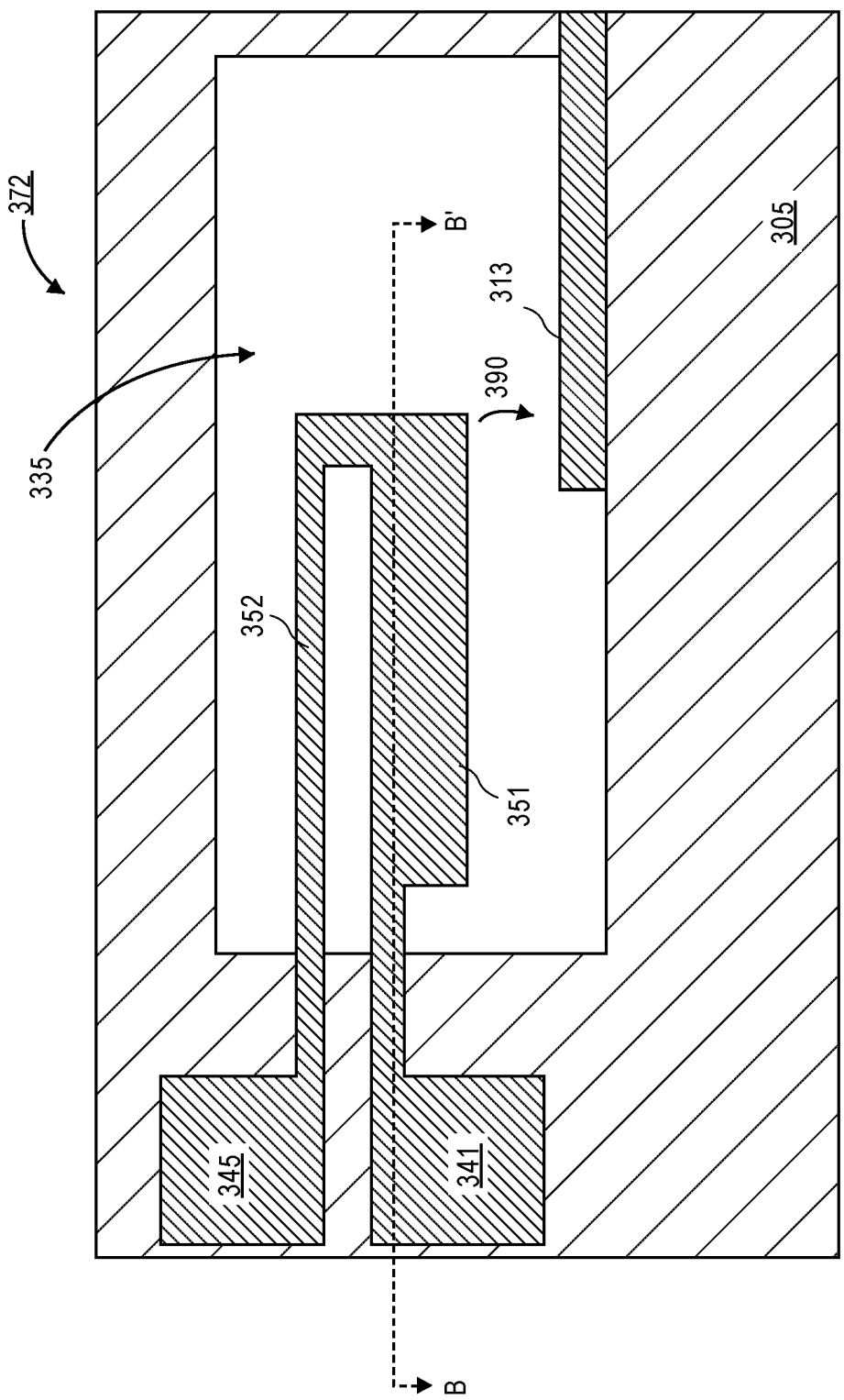

PACKAGE INTEGRATED SECURITY FEATURES

CROSS-REFERENCE TO RELATED APPLICATION

This patent application is a divisional of U.S. patent application Ser. No. 15/283,129, filed on Sep. 30, 2016, the entire contents of which is hereby incorporated by reference herein.

FIELD OF THE INVENTION

Embodiments of the present invention relate generally to integrated security features in a packaging substrate. In particular, embodiments of the present invention relate to a plurality of switches integrated into a package that are used for generating encrypted signals.

BACKGROUND OF THE INVENTION

The rapidly growing Internet of Things (IoT) industry is producing networked devices in many different industries and for many different applications, such as, medical applications, automobiles, smart cities, banking authentication, and physiological health monitoring. The demand for secure, impenetrable data transfer between networked devices is critical. For example, balancing privacy, safety, and security is key in the health industries, particularly for implantable medical devices and body area networks. Accordingly, there has been significant research exploring software enabled security measures and physiological values as an input to cryptographic keys. However, hardware and sensor interfaces may still be targets for malicious attacks.

Currently, a package is hard routed once manufactured and any device attached to the microelectronics has its physical electrical contacts permanently affixed. In some cases fuses may be added to the package. Upon completion of the fabrication of the package, the fuses may be blown to permanently set signal pathways between the devices on the package. Since the data pathways are permanently set, data security enforcement is controlled on the device (e.g., within the die or memory) in conjunction with the preset physical hardware attributes developed during processing (e.g., the unique performance differentials between pairs of circuits at sixty-four different location for one-hundred-twenty-eight bit encryption) and/or in conjunction with software layer protocols that can leverage a plurality of inputs.

However, knowledge of internal hardware and sensor configurations may be used by adversaries to attack the system. For example, sensor systems implicitly trust that physical contact with the sensor is needed to alter the signal, but active attackers may introduce remote interference to sensing in order to affect responses. One such attack may include injecting an electromagnetic signal that mimics a cardiac wave form from centimeters away from a pacemaker. The malicious electromagnetic signal may result in the pacemaker generating an unnecessary therapeutic response, possibly severely harming the user.

BRIEF DESCRIPTION OF THE DRAWINGS

FIG. 3A is a plan view illustration of a thermally actuated switch in an open state, according to an embodiment of the invention.

DETAILED DESCRIPTION OF THE INVENTION

Figure 1A:
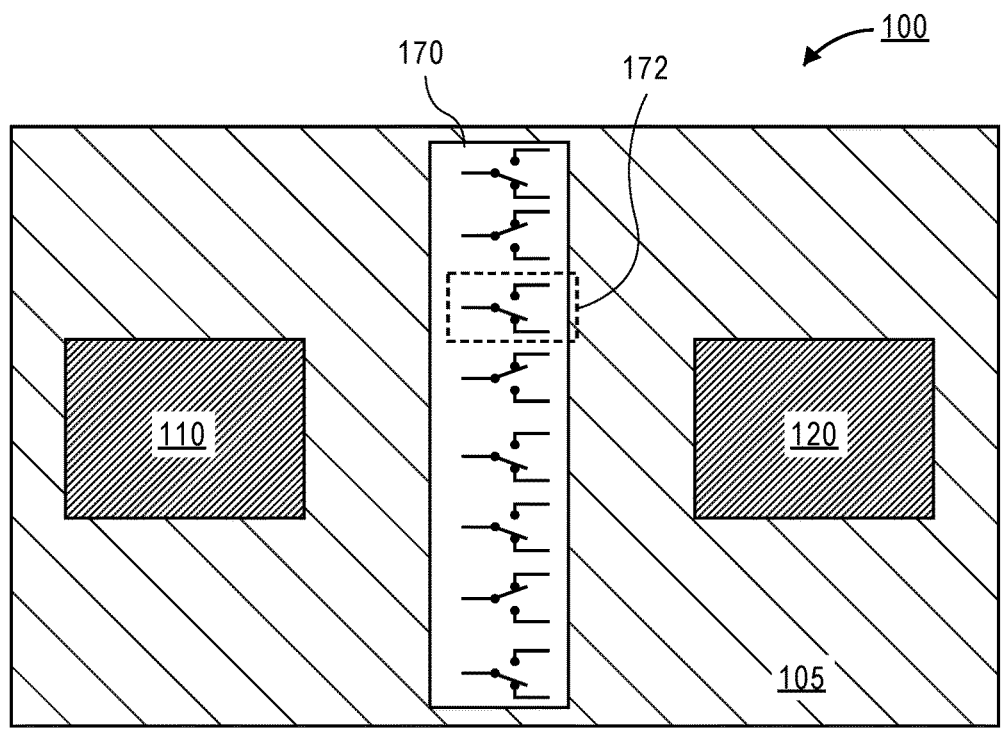
FIG. 1A is a schematic block diagram of a plurality of reconfigurable switches for forming an encryption pathway between components on a package substrate, according to an embodiment of the invention.

Described herein are systems that include a microelectronic package with integrated security features and methods of forming such microelectronic packages. In the following description, various aspects of the illustrative implementations will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative implementations. However, it will be apparent to one skilled in the art that the present invention may be practiced without the specific details. In other instances, well-known features are omitted or simplified in order not to obscure the illustrative implementations.

Various operations will be described as multiple discrete operations, in turn, in a manner that is most helpful in understanding the present invention, however, the order of description should not be construed to imply that these operations are necessarily order dependent. In particular, these operations need not be performed in the order of presentation.

In contrast to the static data pathways described above, embodiments of the invention allow for dynamic switching of the data pathways, thereby increasing the difficulty of hacking the system. According to an embodiment of the invention, switches that are integrated with the microelectronic package allow for the data pathway between components (e.g., sensors, integrated circuits, etc.) on the package to be reconfigurable. The switches may be used by themselves and/or in coordination with other hardware and/or telemetry (e.g., additional physiological inputs), to re-authenticate, re-program and/or re-encrypt sensitive systems or devices. As such, embodiments with switches integrated into the package allow for the microelectronics package itself to be utilized as a security layer.

The inclusion of integrated switches in the microelectronic package may also be used to prevent snooping or gathering of sensitive data from an intruder. This is particularly useful in complex devices (e.g., Systems In Package (SIPs)) where some devices and/or sensors may have local memory holding sensitive information but do not have the ability to detect if that data is being intercepted by an intruder. According to an embodiment, the switches can be reconfigured to provide the intruder with spoofed data or no data and/or provide a way to detect intruders and the location of their hardware attack. Furthermore, the integrated switches may be used in conjunction with sensor data to provide an additional security layer for determining whether data received from a sensor is valid or spoofed. For example, data from multiple sensor types (e.g., heart rate, heart arrhythmias, shortness of breath, upper body pain, blood pressure, blood chemistry, body temperature, sweat) may be used together to understand whether a human is really experiencing a cardiac excursion or not. Only when each of the multitude of physiological inputs indicate that a cardiac excursion is occurring and each sensor signal is properly encrypted, will the system initiate a cardiac electrical stimulus.

Embodiments of the invention may also ensure no single point of failure of key devices by enabling redundancy without requiring additional power consumption. For example, multiple data pathways may be fabricated and a switch may be used to alter the route if one of the pathways is damaged.

Referring now to FIG. 1A, a schematic plan view of a microelectronics package 100 is illustrated, according to an embodiment of the invention. In an embodiment, the microelectronics package 100 may include a first electrical component 110 and a second electrical component 120. The first component 110 may be any electrical device or sensor that includes a local memory for storing data and/or is able to generate data. For example, the first component may be a physiological sensor, such as a sensor for detecting heart rate, heart arrhythmias, shortness of breath, upper body pain, blood pressure, blood chemistry, body temperature, sweat, or the like. In an embodiment, the second electrical component 120 may be any device that utilizes the data produced or stored on the first component 110. For example, the second component 120 may be a processor, system on a chip (SoC), or the like.

According to an embodiment of the invention, data may be transferred from the first electrical component 110 to the second electrical component 120 by one or more transmission lines (not shown). In order to provide secure transmission of data between the first component 110 and the second component 120, embodiments of the invention may include a reconfigurable encryption bank 170 along the data transmission path between the first component 110 and the second component 120. According to an embodiment, the reconfigurable encryption bank 170 may include a plurality of switches 172. The plurality of switches 172 in the reconfigurable encryption bank 170 may be switched to different positions by a random number generator or an impulse generator to provide a unique encryption pathway between the first component 110 and the second component 120. Increasing the number of switches 172 in the reconfigurable encryption bank 170 increases the strength of the encryption. For example, a combination of sixteen switches 172 may provide a thirty-two bit encryption by providing sixteen unique pathways between the first component 110 and the second component 120. While the switches 172 are shown in parallel, any configuration may be used. For example, switches 172 may be connected in series and/or in parallel, depending on the needs of the device. In the illustrated embodiment, the switches are each shown as being in one of two states (e.g., connected to an upper trace or a lower trace). However, embodiments may include switches 172 that can be in an open configuration (e.g., not connected to the upper or lower trace) as well.

According to an embodiment, changing the configuration of a switch 172 may result in a change in the latency of the data pathway. The different latencies provided by the unique pathways may be used to ensure that signals delivered between the first component 110 and the second component 120 are authentic. For example, for any given configuration of the switches 172, there will be a known latency pattern that can serve as a token that proves the authenticity of the data. Attempts at sending falsified data to the second electrical component 120 by an intruder may be recognized by the system because the latencies in the falsified data will not match the expected latencies that would be produced by the random configuration of the switches 172. In such cases, the microelectronic package 100 will know that an unauthorized user is trying to compromise the system. In order to prevent an intruder from discovering the latency patterns produced by the switches, embodiments may also include a random number generator that is used to reconfigure the switches 172 periodically. In an embodiment, the switches 172 in the reconfigurable encryption bank 170 may be re-programed at regular intervals, at random intervals, when an intruder is detected, and/or at any desired time.

Figure 1B:
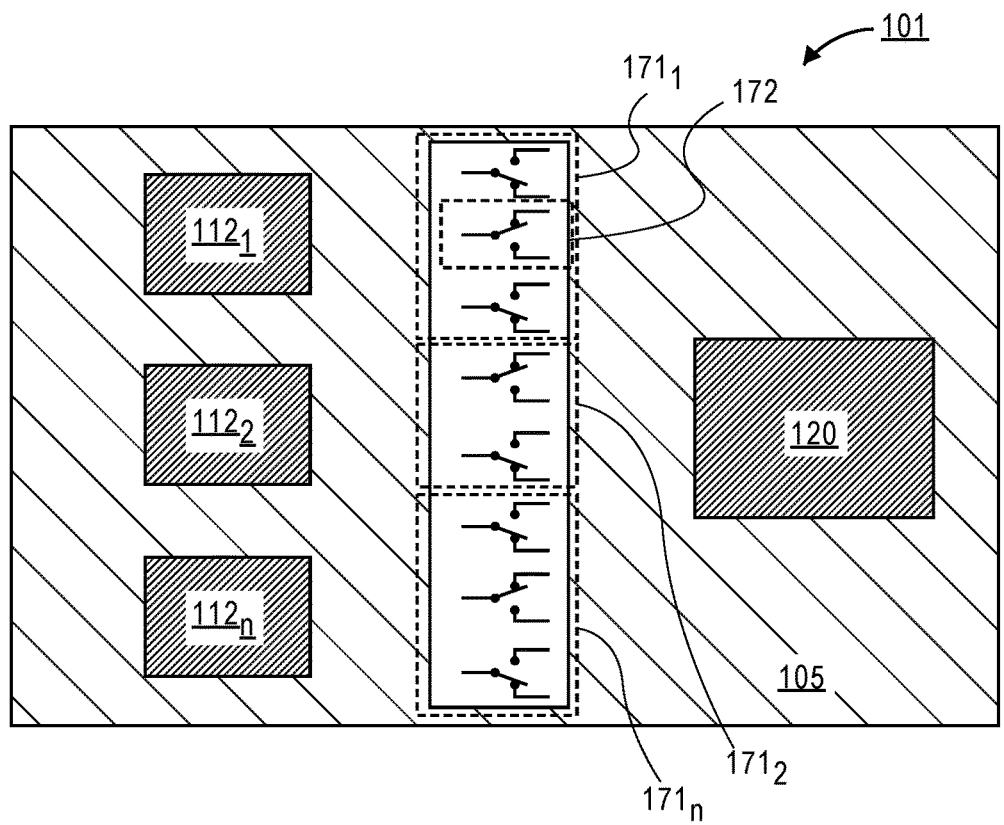
FIG. 1B is a schematic block diagram of a plurality of reconfigurable switches for forming an encryption pathway between sensors and an integrated circuit, according to an embodiment of the invention.

Additional embodiments of the invention may also include a plurality of first components that each deliver encrypted signals to the second component. Such embodiments may be useful for systems that include a plurality of sensors that deliver information to a second component. FIG. 1B provides an example of such a system according to an embodiment of the invention.

Referring now to FIG. 1B, a schematic plan view of a microelectronics package 101 that includes a plurality of sensors 112 is illustrated, according to an embodiment of the invention. In an embodiment, the microelectronics package 101 may include a plurality of sensors 112 and a second electrical component 120. Each of the plurality of sensors 112 may be any electrical device or sensor that includes a local memory for storing data and/or is able to generate data. For example, each of the plurality of sensors 112 may be a physiological sensor, such as a sensor for detecting heart rate, heart arrhythmias, shortness of breath, upper body pain, blood pressure, blood chemistry, body temperature, sweat, or the like. While three sensors $112_{1-n}$ are illustrated, embodiments are not limited to such configurations, and any number of sensors 112 may be used. In an embodiment, the second electrical component 120 may be any device that utilizes the data produced or stored by each of the sensors 112. For example, the electrical component 120 may be a processor, SoC, or the like. Additionally, while a single second electrical component 120 is shown, embodiments are not limited to such configurations, and any number of second electrical components 120 may be used.

According to an embodiment, each of the sensors $112_{1-n}$ transmit data through different portions $171_{1-n}$ of the reconfigurable encryption bank 170. In the illustrated embodiment, two of the portions $171_1$ and $171_n$ have three switches 172, and one of the portions $171_2$ includes two switches 172, though embodiments are not limited to such configurations. For example, each portion 171 may include one or more switches 172. Additionally, embodiments may include the same number of switches 172 in each portion 171.

Since each sensor 112 has a dedicated encryption path, embodiments of the invention enable the detection of when a particular one of the sensors 112 may be compromised. For example, if data received from sensors $112_1$ and $112_2$ include latency patterns that match the configuration of the switches in portions $171_1$ and $171_2$, respectively, but data received from sensor $112_n$ does not match the expected latency pattern for the configuration of switches in portion $171_n$, then it can be assumed that an intruder to the system has compromised sensor $112_n$ and is providing falsified data. According to an embodiment, falsified data may be ignored by the second component 120. Alternative embodiments may also include responding to falsified data by sending back misleading data to the intruder. For example, the misleading data may be used to prevent future attacks, or function as a trap to allow the identity of the intruder to become known to the user, authorities, or the like.

Similar to the device described in FIG. 1A, embodiments of the invention may allow for each portion $171_{1-n}$ to be re-programmed at regular intervals or randomly. The portions $171_{1-n}$ may all be re-programed at the same time. Alternatively, the portions $171_{1-n}$ may be re-programmed individually. For example, if it is determined that falsified data is being received from one sensor, then that portion 171 of the encryption bank 170 may be re-programmed more frequently.

In addition to encrypting communication between the sensors 112 and the second component 120 with the encryption bank 170, embodiments may also include an additional layer of security that requires a plurality of signals between the plurality of sensors 112 and the second component 120 to each be properly encrypted and indicative of a predetermined condition before a response is initiated. Such an embodiment may be particularly beneficial for systems that have high security requirements. For example, implantable medical devices (e.g., pacemakers) may be particularly high risk security targets. If a malicious signal were sent to the pacemaker, an unnecessary therapeutic response may be delivered. Accordingly, embodiments of the invention may include a second component 120 that determines whether the predetermined condition is occurring (or has occurred) based on the output from each of the sensors 112, and also requires proper encryption for each of the output signals from the sensors 112. Only then, will the second component initiate a response to the predetermined condition. For example, when the predetermined condition is a heart attack, the response may be an electrical shock that is used to mitigate the effects of the heart attack.

In the example of a pacemaker, the system may include sensors 112 for detecting heart rate, sweat, and body temperature. During a true heart attack, the heart rate, sweat, and body temperature should all increase since they are each indicative of the occurrence of a heart attack. As such, if the second component 120 only receives a signal that the heart rate was increasing while the data from the sweat and body temperatures remained normal, then it may be determined by the second component 120 that the heart rate increase data is a malicious signal. Accordingly, even if the heart rate sensor 112 delivered a signal with latencies that match the expected latencies determined by the switches 172, it may be determined that the signal is still malicious. In such embodiments, the malicious signal may be ignored. Alternatively, the configuration of the switches 172 may be changed in order to determine if subsequent signals from the heart rate sensor 112 match the new latency pattern after the change to the switches have been made. When subsequent signals from the heart rate sensor 112 do not match the updated switch configuration, then it may be determined that the original signal was malicious.

According to embodiments of the invention, switches 172 used in the encryption bank 170 may be integrated directly into the package substrate 105. Accordingly, the form factor of the package 100 is not greatly increased. Additionally, embodiments of the invention include switches that may be fabricated with standard package fabrication processes. In one embodiment the switches 172 may be piezoelectrically driven. An example of a piezoelectrically driven switch that is integrated in the substrate is described with respect to FIGS. 2A-2E.

Figure 2A:
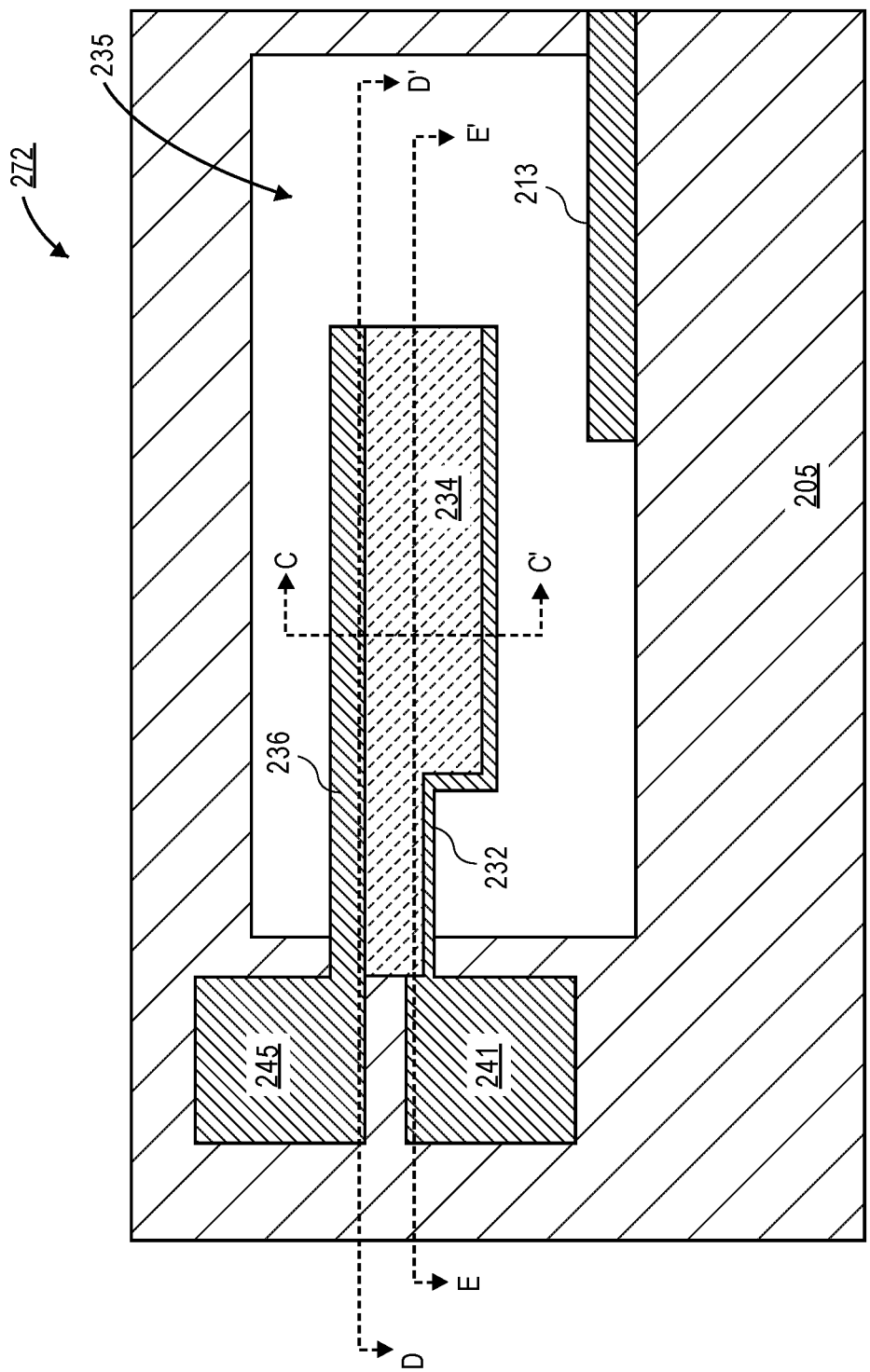
FIG. 2A is a plan view illustration of a piezoelectrically actuated switch in an open state, according to an embodiment of the invention.
Figure 2B:
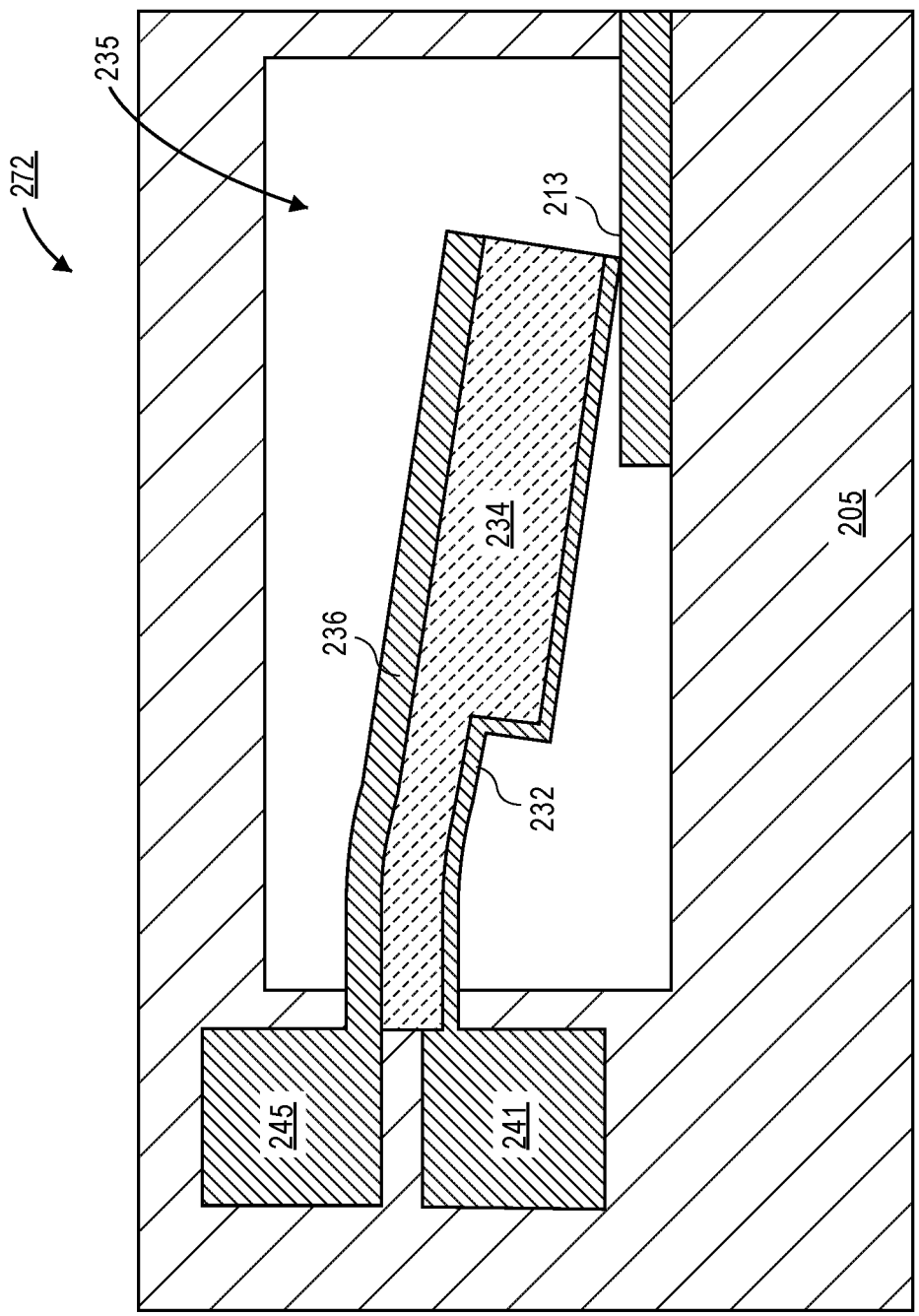
FIG. 2B is a plan view illustration of the piezoelectrically actuated switch in a closed state, according to an embodiment of the invention.

Referring now to FIG. 2A, a plan view illustration of a piezoelectrically driven switch 272 that may be used in an encryption bank is shown, according to an embodiment of the invention. In an embodiment, the switch 272 may be a piezoelectric switch 272 that is actuatable in the plane of the substrate 205. Accordingly, the switch 272 may be deflected so that it contacts a conductive trace 213 and completes a circuit between a sensor and electrical component (not shown). In the unactuated state, as shown in FIG. 2A, the circuit may be open.

In an embodiment of the invention, the switch 272 may include a first electrode 232 and a second electrode 236 that is separated from the first electrode 232 by a piezoelectric material 234. In order to provide deflection in the plane of the substrate 205, the first electrode 232 and the second electrode 236 may be formed along opposing sidewall surfaces of the piezoelectric material 234. In such embodiments, applying a voltage across the piezoelectric material 234 may result in the piezoelectric material 234 deflecting towards conductive trace 213, as illustrated in the plan view in FIG. 2B. Additionally, a non-uniform cross-section of the piezoelectric material 234 may be used to enhance the amount of deflection attainable by the switch 272.

In order to provide free movement of the switch 272, the switch 272 may be oriented so that the first and second electrodes 232, 236 and the piezoelectric material 234 form a beam that extends over a cavity 235 formed in the substrate 205. Since the beam is not constrained from below by the substrate 205, the beam is free to move when the piezoelectric material 234 is strained when a voltage differential is applied between the first electrode 232 and the second electrode 236. According to an additional embodiment, the switch 272 may also be embedded within the substrate 205.

In such an embodiment, the switch 272 may be anchored to the substrate 205 and extend out from a sidewall of the cavity 235. An embedded switch 272 may be fabricated in one layer and be surrounded by sacrificial materials or utilize pre-fabrication lamination techniques in order to maintain void space integrity and enable mechanical motion without friction or jamming.

While a switch 272 is only shown in a single layer in FIG. 2A, it is to be appreciated that switches 272 may be formed in multiple layers of the substrate 205, according to additional embodiments of the invention. For example, two or more switches 272 may be stacked over each other in different layers. As such, a greater number of switches may be formed without increasing the footprint of the encryption bank. Additionally, the switch 272 is shown as a single beam that is deflected towards a trace 213, though embodiments are not limited to this configuration. For example, it is to be appreciated that multiple actuatable beams may be used in conjunction with each other to form tri- or bi-stable mechanical switches. Examples of such switches are described in greater detail below with respect to FIGS. 5A-5C.

According to an embodiment, the first electrode 232 and the second electrode 236 may be anchored to the substrate 205 by a first anchor 241 and a second anchor 245, respectively. The first and second anchors 241, 245 may electrically couple the first and second electrodes 232, 236 to a voltage source (not shown). As such, a voltage differential across the first electrode 232 and the second electrode 236 may be generated. The voltage applied across the first electrode 232 and the second electrode 236 induces a strain in the piezoelectric layer 234 that causes displacement of the switch 272. In an embodiment, the displacement of the switch 272 is proportional to the voltage across the first electrode 232 and the second electrode 236.

According to an embodiment, the first electrode 232 and the second electrode 236 are formed with a conductive material. In some embodiments, the first electrode 232 and the second electrode 236 may be formed with the same conductive material used to form the conductive traces, vias, and pads formed in the substrate 205. Such an embodiment allows for the manufacture of the microelectronic package to be simplified since additional materials are not needed, though embodiments are not limited to such configurations. For example, the electrodes 232, 236 may be different materials than the traces. Additional embodiments may include a first electrode 232 that is a different material than the second electrode 236. The conductive material used for the first electrode 232 and the second electrode 236 may be any conductive material (e.g., copper, aluminum, alloys, etc.).

Embodiments of the invention include a high performance piezoelectric material for the piezoelectric layer 234. For example, the high performance piezoelectric layer 234 may be lead zirconate titanate (PZT), potassium sodium niobate (KNN), zinc oxide (ZnO), or combinations thereof. High performance piezoelectric materials such as these typically require a high temperature anneal (e.g., greater than 500° C.) in order to attain the proper crystal structure to provide the piezoelectric effect. As such, currently available piezoelectric actuators require a substrate that is capable of withstanding high temperatures (e.g., silicon). Low melting temperature substrates described herein, such as organic substrates, typically cannot withstand temperatures above 260° C. However, embodiments of the present invention allow for a piezoelectric layer 234 to be formed at much lower temperatures. For example, instead of a high temperature anneal, embodiments include depositing the piezoelectric layer 234 in an amorphous phase and then using a pulsed laser to crystalize the piezoelectric layer 234. For example, the piezoelectric layer 234 may be deposited with a sputtering process, an ink jetting process, or the like. According to an embodiment, the pulsed laser annealing process may use an excimer laser with an energy density between approximately 10-100 mJ/cm$^2$ and a pulse width between approximately 10-50 nanoseconds. Utilizing such an annealing process allows for the high performance piezoelectric layer 234 to be formed without damaging the substrate 205 on which the switch 272 is formed.

Figure 2C:
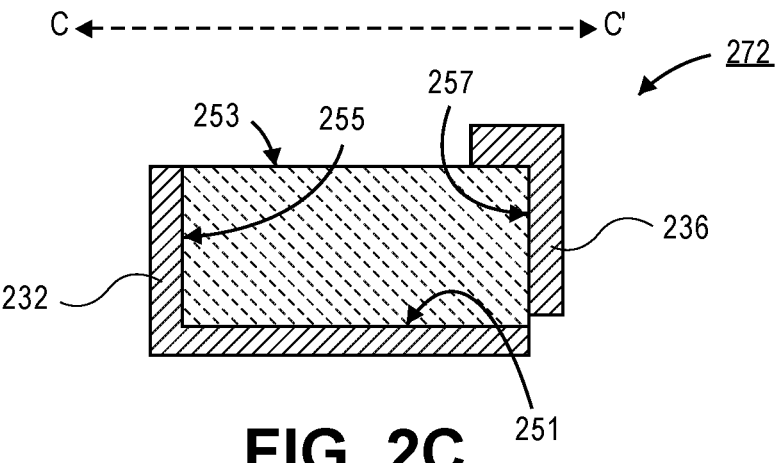
FIG. 2C is a cross-sectional illustration of the piezoelectrically actuated switch in FIG. 2A along line C-C', according to an embodiment of the invention.

Referring now to FIG. 2C, a cross-sectional illustration of a portion of the switch 272 along line C-C' in FIG. 2A is shown, according to an embodiment of the invention. The cross-sectional view provides an example of how the piezoelectric layer 234 is supported between the first electrode 232 and the second electrode 236. In order to allow for actuation in the plane of the substrate 205, portions of the first electrode 232 are formed along a first sidewall 255 of the piezoelectric material 234 and portions of the second electrode 236 are formed along a second sidewall 257 that is opposite the first sidewall 255. In some embodiments, a portion of the first electrode 232 may be formed below a bottom surface 251 of the piezoelectric material 234. The portion of the first electrode 232 below the piezoelectric material 234 provides a support structure that may be used as a surface on which the piezoelectric material 234 is deposited during the formation of the switch 272. In some embodiments, an insulative material (not shown) may be deposited over the portion of the first electrode 232 in order to provide an electrical field primarily oriented in the horizontal plane. Similarly, an insulative layer (not shown) may be formed over a top surface 253 of the piezoelectric material 234 in order to prevent portions of the second electrode 236 from contacting the piezoelectric material 234.

Figure 2D:
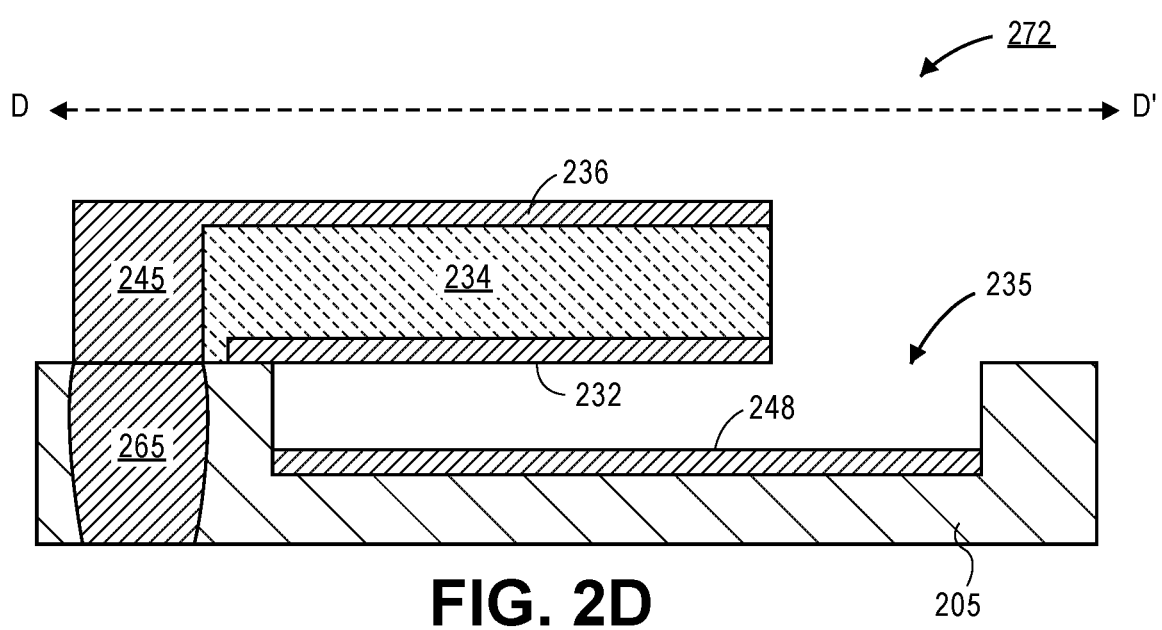
FIG. 2D is a cross-sectional illustration of the piezoelectrically actuated switch in FIG. 2A along line D-D', according to an embodiment of the invention.
Figure 2E:
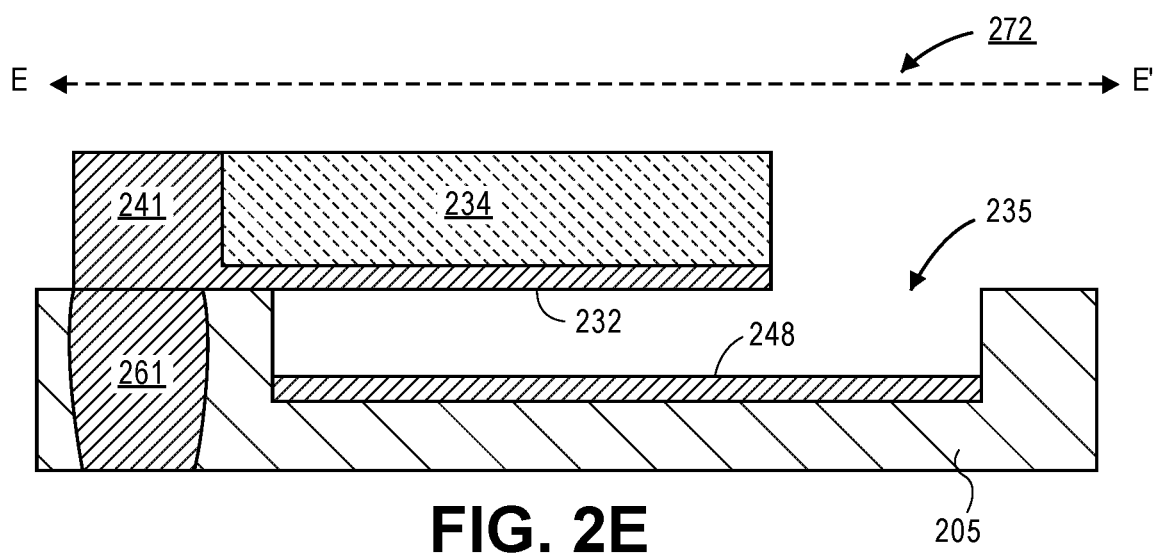
FIG. 2E is a cross-sectional illustration of the piezoelectrically actuated switch in FIG. 2A along line E-E', according to an embodiment of the invention.

Referring now to FIGS. 2D and 2E, cross-sectional illustrations of portions of the switch 272 are shown along lines D-D' and E-E' in FIG. 2A, respectively, according to an embodiment of the invention. In FIG. 2D the cross-section illustrates a portion of the second electrode 236 formed over a top surface of the piezoelectric material 234 and electrically coupled to the second anchor 245. The second anchor 245 may also be coupled to pads, traces, and/or vias 265 formed in or on the substrate 205. In the illustrated embodiment, the second anchor 245 and the via 265 are illustrated as distinct regions, however embodiments are not limited to such configurations. For example, there may not be a discernable difference between the second anchor 245 and the vias 265. Additionally, the first electrode 232 is shown supporting the piezoelectric material 234 from below. According to an embodiment, the first electrode 232 may be electrically isolated from the second electrode 236 and the second anchor 245 by a portion of the piezoelectric material 234 that is formed over a surface of the substrate 205. Alternative embodiments may also include an insulative material (not shown) being formed between the first electrode 232 and the second electrode 236 and/or the second anchor 245.

Referring now to FIG. 2E, the cross-sectional illustration shows the connection between the first electrode 232 and the first anchor 241. According to an embodiment, the first electrode 232 extends substantially along the entire length of the piezoelectric material 234 in order to provide a surface on which the piezoelectric material 234 may be deposited.

Additionally, as illustrated in FIGS. 2D and 2E, an etchstop layer 248 may be formed at the bottom surface of the cavity 235, according to some embodiments of the invention. An etchstop layer 248 may be used to enable a controlled etching process that provides a precise and uniform depth for the cavity 235. In an embodiment, the etchstop layer 248 may be any suitable material that is resistant to an etching process used to form the cavity 235. In some embodiments, the etchstop layer 248 may be the same material as the electrodes or other conductive features formed in the substrate 205.

While a piezoelectrically actuated switch is described above, embodiments are not limited to such configurations. For example, some embodiments may also include switches that are driven by thermal expansion. An example of such a switch is illustrated and descried with respect to FIGS. 3A and 3B.

Figure 3B:
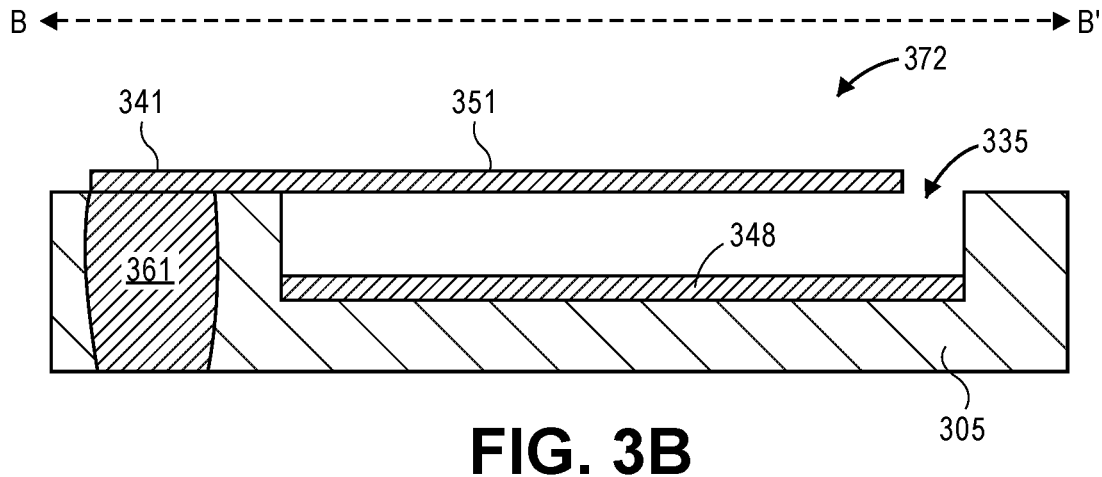
FIG. 3B is a cross-sectional illustration of the thermally actuated switch, according to an embodiment of the invention.

Referring now to FIGS. 3A and 3B, a plan view illustration and a corresponding cross-sectional illustration along line B-B' of a switch are shown, according to an additional embodiment of the invention. In order to provide free movement of the switch 372, the switch 372 may be oriented so that a first portion 351 and a second portion 352 of the switch 372 extend over the cavity 335 formed in the substrate 305. Since the first portion 351 and the second portion 352 are not constrained from below by the substrate 305, the switch 372 is free to move when the current is supplied. According to an additional embodiment, the switch 372 may also be embedded within the substrate 305. In such an embodiment, the switch 372 may be anchored to the substrate 305 and the first portion 351 and the second portion 352 may extend out from a sidewall of the cavity 335. An embedded switch 372 may be fabricated in one layer and be surrounded by sacrificial materials or utilize pre-fabrication lamination techniques in order to maintain void space integrity and enable mechanical motion without friction or jamming.

While a switch 372 is only shown in a single layer in FIG. 3A, it is to be appreciated that actuators may be formed in multiple layers of the substrate 305, according to additional embodiments of the invention. For example, two or more switches 372 may be stacked over each other in different layers. As such, a greater number of switches may be formed without increasing the footprint of the encryption bank. Additionally, the switch 372 is shown as a single beam that is deflected towards a trace 313, though embodiments are not limited to this configuration. For example, it is to be appreciated that multiple actuatable beams may be used in conjunction with each other to form tri- or bi-stable mechanical switches. Examples of such switches are described in greater detail below with respect to FIGS. 5A-5C.

According to an embodiment, the first portion 351 of the beam and the second portion 352 of the beam may be anchored to the to the substrate 305 by a first anchor 341 and a second anchor 345, respectively. The first and second anchors 341, 345 may electrically couple the switch 372 to a power source (not shown). As such, an electrical current may pass through the first portion 351 and second portion 352 of the switch 372.

Instead of relying on piezoelectric actuation, the switch 372 may rely on temperature differences between a first portion 351 and a second portion 352 of switch 372 in order to provide actuation. Specifically, resistive heating occurs as current passes through the first portion 351 and second portion 352 of the switch 372. According to an embodiment, the change in temperature of each portion is controlled by changing the cross-sectional area of each portion of the switch 372. For example, the first portion 351 may have a larger cross-sectional area than the second portion 352. Accordingly, the second portion 352 will experience a greater increase in temperature than the first portion 351, thereby resulting in greater thermal expansion. The greater thermal expansion in the second portion 352 causes the beam to deflect towards the conductive trace 313, as indicated by arrow 390.

In FIG. 3B, the cross-sectional illustration shows the connection of the switch 372 to an anchor 341. The anchor 341 may be substantially similar to the anchors 241/245 described above. Accordingly, the anchor 341 may include vias 361 formed into the substrate 305 that are electrically coupled to an electrical circuit that allows for current to pass through the first and second portions 351, 352 of the switch 372. Additionally, since switch 372 does not need to support a piezoelectric layer or provide electrical contact to sidewalls of a piezoelectric layer, the thickness of the first portion 351 and the second portion 352 may be substantially uniform, though embodiments are not limited to such configurations. For example, the extent of resistive heating in each portion may be controlled by providing a greater thickness in one portion in order to provide less resistive heating in the thicker portion.

Additionally, an etchstop layer 348 may be formed at the bottom surface of the cavity 335, according to some embodiments of the invention. An etchstop layer 348 may be used to enable a controlled etching process that provides a precise and uniform depth.

In addition to switches that are actuatable in the plane of the substrate, embodiments of the invention may also include switches that are actuatable out of the plane of the substrate. An example of one such switch is illustrated with respect to FIGS. 4A-4C.

Figure 4A:
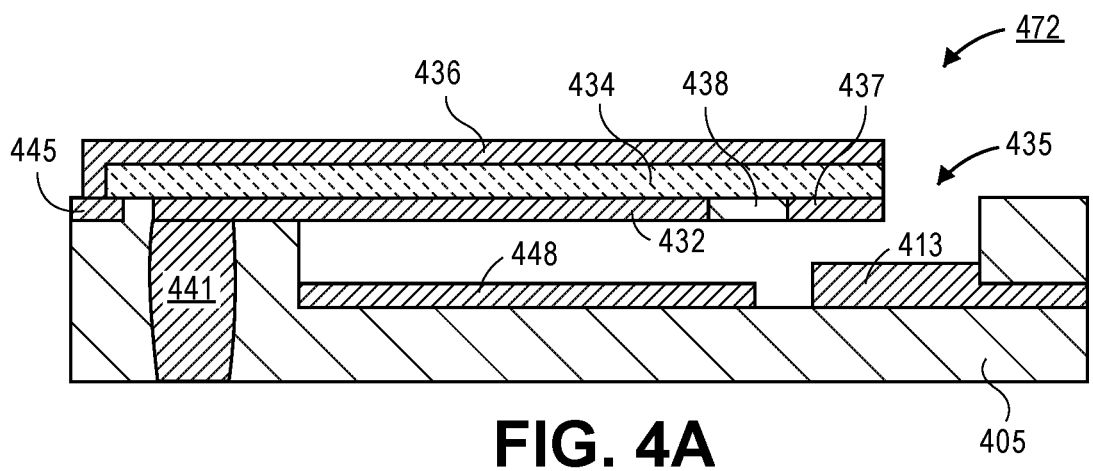
FIG. 4A is a cross-sectional illustration of a piezoelectrically actuated switch that is actuatable out of the plane of the substrate in an open state, according to an embodiment of the invention.

Referring now to FIG. 4A, a cross-sectional illustration of a piezoelectrically driven switch 472 is shown in an unactuated state, according to an embodiment of the invention. As illustrated, the switch 472 may be anchored to the substrate 405 and oriented so that it extends over the cavity 435 formed in the substrate 405. According to an embodiment, the substrate 405 may also include one or more conductive traces 413 to provide electrical routing in the substrate 405.

According to an embodiment, the switch 472 includes a piezoelectric layer 434 formed between a first electrode 432 and a second electrode 436. According to an embodiment, the piezoelectric layer 434 may be a high performance piezoelectric material, similar to those described above. For example, the high performance piezoelectric layer 434 may be PZT, KNN, ZnO, or combinations thereof. Additionally, the high performance piezoelectric layer 434 may be formed with a pulsed laser annealing process similar to the processing operations described above.

The first electrode 432 and the second electrode 436 may be electrically coupled to a voltage source by conductive traces and/or anchors 445, 441 formed in substrate 405. As such, a voltage applied across the first electrode 432 and the second electrode 436 may be generated. The voltage applied across the first electrode 432 and the second electrode 436 induces a strain in the piezoelectric layer 434 that causes displacement of the switch 472. In an embodiment, the displacement of the switch 472 is proportional to the voltage across the first electrode 432 and the second electrode 436, as will be described in greater detail below.

According to an embodiment, the first electrode 432 and the second electrode 436 are formed with a conductive material. In some embodiments, the first electrode 432 and the second electrode 436 may be formed with the same conductive material used to form the other conductive features that are formed in the substrate 405. Such an embodiment allows for the manufacturing of the microelectronic package to be simplified since additional materials are not needed, though embodiments are not limited to such configurations.

According to an embodiment, a bridge trace 437 may also be formed on the switch 472. In an embodiment, the bridge trace 437 is electrically isolated from the first electrode 434 by an insulating material 438. For example, the insulating material may be the same material as the substrate, or any other suitable insulating material, (e.g., an oxide, nitride, polymer, etc.). The bridge trace 437 may be used to complete a circuit with the conductive traces 413 when the switch 472 is actuated. Referring briefly to the plan view in FIG. 4C, a first trace $413_A$ and a second trace $413_B$ are formed in the cavity and electrically isolated from each other when the switch 472 is not actuated. Upon actuation, the bridge trace 437 formed on the bottom surface of the switch 472 may provide a conductive bridge between the first trace $413_A$ and the second trace $413_B$.

Figure 4B:
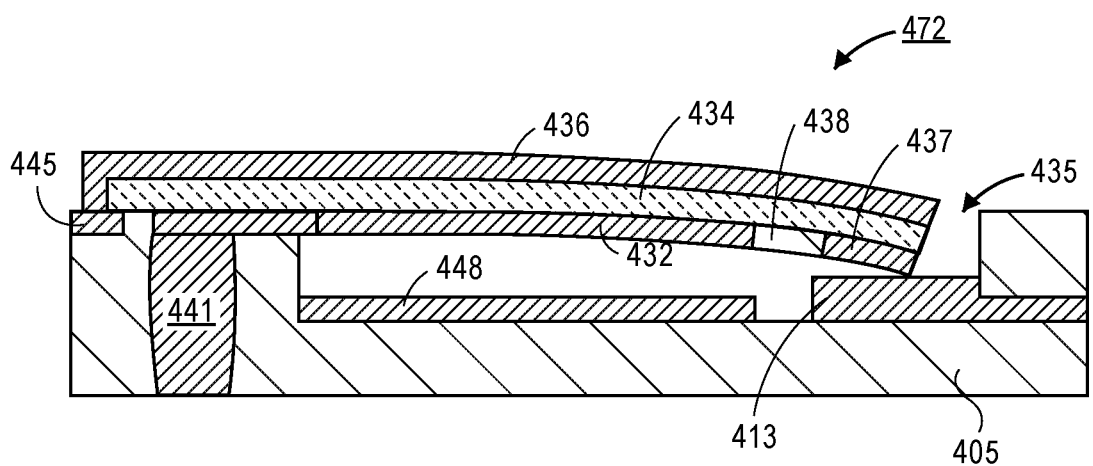
FIG. 4B is a cross-sectional illustration of the piezoelectrically actuated switch that is actuatable out of the plane of the substrate in a closed state, according to an embodiment of the invention.
Figure 4C:
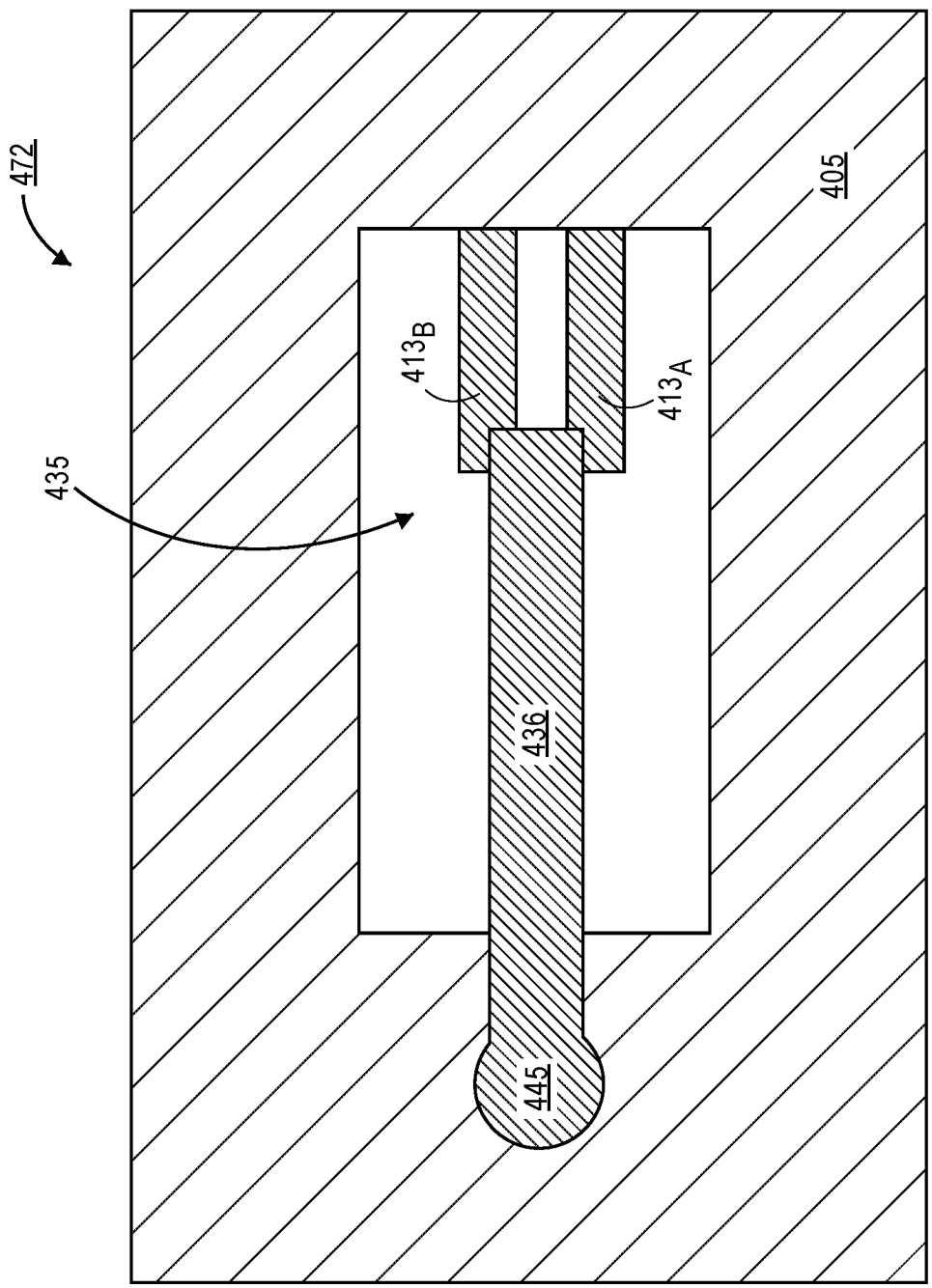
FIG. 4C is a plan view illustration of the piezoelectrically actuated switch that is actuatable out of the plane of the substrate, according to an embodiment of the invention.

Referring now to FIG. 4B, a cross-sectional illustration of the switch 472 in an actuated state is shown, according to an embodiment of the invention. The switch 472 may be displaced by applying a voltage across the first electrode 432 and the second electrode 436. The voltage produces strain in the piezoelectric layer 434 that causes the switch 472 to displace out of plane of the substrate 405. Accordingly, the bridge trace 437 is brought into contact with the traces 413 in the cavity 435 to complete the circuit.

The above examples describe switches where the actuation takes place upon energizing the piezoelectric layers or generating thermal expansion. In such embodiments, the power needs to be continuously held in order to maintain the deflection of the switch. However, it is to be appreciated that some embodiments of the invention may further include a bi- or tri-stable switch arrangement such that, upon charge, the switch is shifted and held and conversely, charged again to move back to the original position. Additionally, in some embodiments, the process may be driven in reverse to release the actuation of the switch. Accordingly, the actuated states may be maintained even when the power is removed, thereby reducing the overall system power.

Figure 5A:
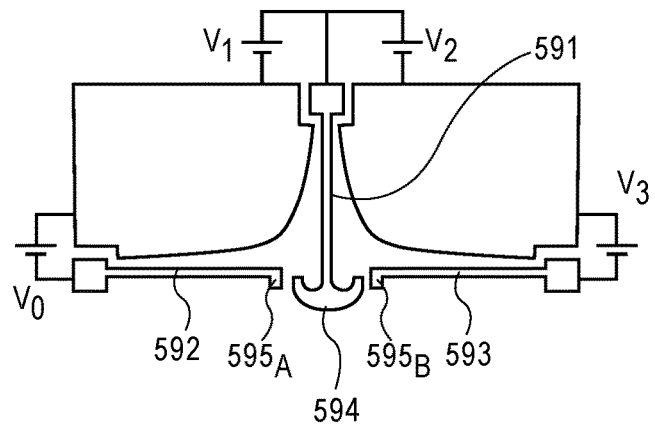
FIG. 5A is a schematic illustration of a mechanically tri-stable switch that is in a first position, according to an embodiment of the invention.
Figure 5B:
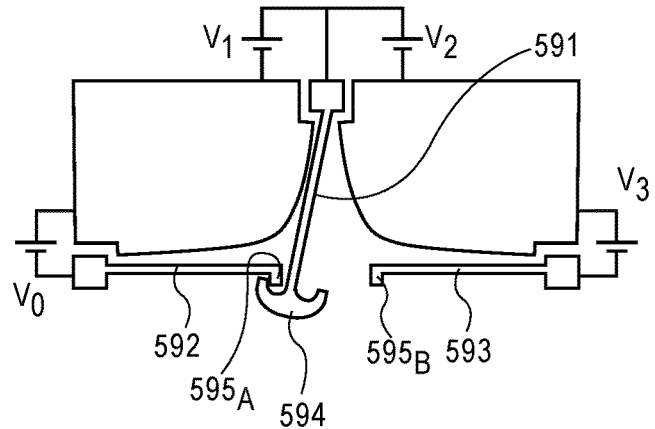
FIG. 5B is a schematic illustration of a mechanically tri-stable switch that is in a second position, according to an embodiment of the invention.
Figure 5C:
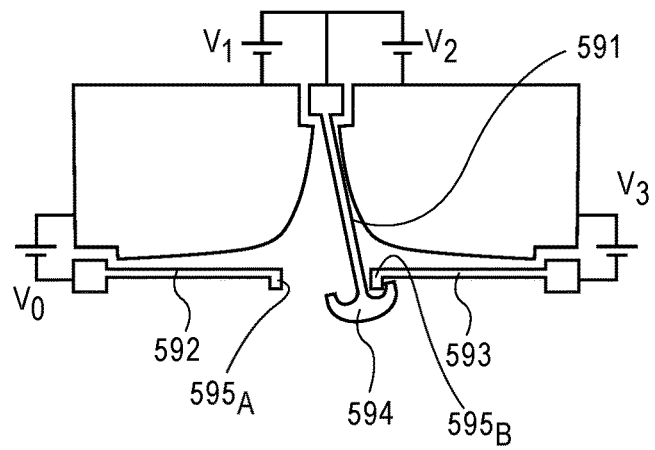
FIG. 5C is a schematic illustration of a mechanically tri-stable switch that is in a third position, according to an embodiment of the invention.

A schematic illustration of an example of one suitable tri-stable mechanical state switch that may be used according to embodiments of the invention is described with respect to FIGS. 5A-5C. While one example is shown, it is to be appreciated that embodiments of the invention may use any bi- or tri-stable mechanical state switch. In an embodiment, the actuation mechanism of the bi- or tri-stable switch may be driven by piezoelectric actuation or thermal expansion, similar to the embodiments described above.

As illustrated, the switch may be open (FIG. 5A), in a second position (FIG. 5B), or in a third position (FIG. 5C). According to an embodiment, the switch 591 is mechanically held in the second and third positions by a mechanical anchor 594. For example in FIG. 5B, the anchor 594 of the switch 591 is locked on to an end piece $595_A$ of beam 592. Similarly, in FIG. 5C, the anchor 594 of the switch 591 is locked on to an end piece $595_B$ of beam 593.

In order to cause the anchor 594 to lock into either position (or be removed from the locked position) the switch 591 and the beam (592 or 593 depending on the position to which the switch 591 is being actuated) are actuated (e.g., with piezoelectric actuation or thermal expansion actuation substantially similar to the switches described according to embodiments of the invention) sequentially to bring the anchor 594 and the end piece 595 into contact. For example, beam 592 may be actuated so that the beam 592 is deflected upwards. Thereafter, the switch 591 may be actuated so that the anchor 594 is deflected under the end piece $595_A$ of beam 592. Once in position, the voltage applied to beam 592 may be removed, to allow beam 592 to return to a neutral position. However, the anchor 594 catches and secures the end piece $595_A$, preventing the full return back to the neutral position. After the end piece $595_A$ and the anchor 594 are secured to each other, the voltage to the switch 591 may be released since the switch 591 is prevented from returning back to the neutral position.

In order to release switch 591 and allow it to return to the neutral position, the beam 592 may be deflected upwards by applying a voltage, thereby disengaging the end piece $595_A$ from the anchor 594. Since the voltage has been removed from the switch 591, the switch 591 may return to the neutral position and the voltage to beam 592 may also be released allowing beam 592 to return to the neutral position as well. A similar sequence may be used to cause the switch 591 to be secured to or released from beam 593.

Figure 6:
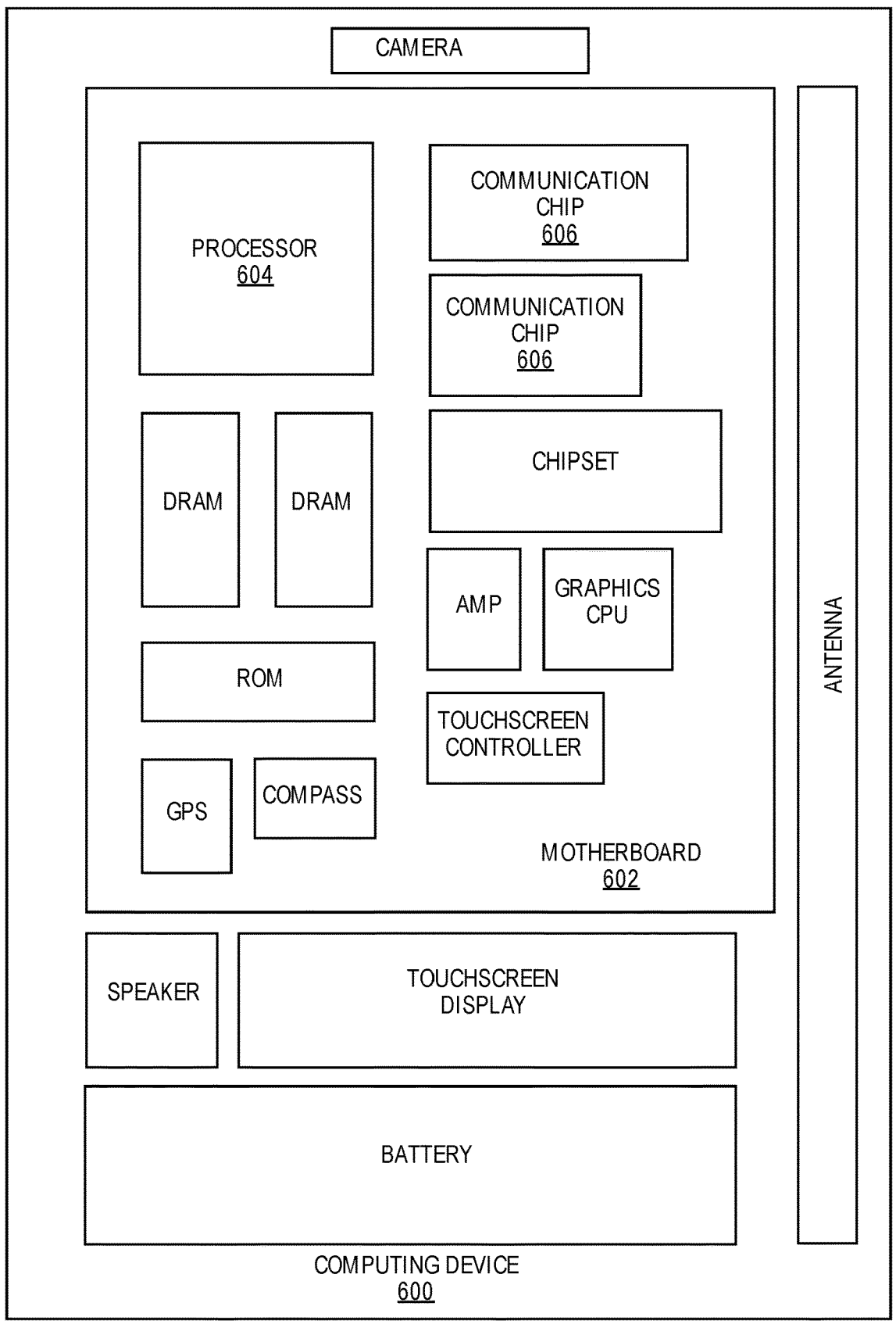
FIG. 6 is a schematic of a computing device built in accordance with an embodiment of the invention.

FIG. 6 illustrates a computing device 600 in accordance with one implementation of the invention. The computing device 600 houses a board 602. The board 602 may include a number of components, including but not limited to a processor 604 and at least one communication chip 606. The processor 604 is physically and electrically coupled to the board 602. In some implementations the at least one communication chip 606 is also physically and electrically coupled to the board 602. In further implementations, the communication chip 606 is part of the processor 604.

Depending on its applications, computing device 600 may include other components that may or may not be physically and electrically coupled to the board 602. These other components include, but are not limited to, volatile memory (e.g., DRAM), non-volatile memory (e.g., ROM), flash memory, a graphics processor, a digital signal processor, a crypto processor, a chipset, an antenna, a display, a touchscreen display, a touchscreen controller, a battery, an audio codec, a video codec, a power amplifier, a global positioning system (GPS) device, a compass, an accelerometer, a gyroscope, a speaker, a camera, and a mass storage device (such as hard disk drive, compact disk (CD), digital versatile disk (DVD), and so forth).

The communication chip 606 enables wireless communications for the transfer of data to and from the computing device 600. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communication chip 606 may implement any of a number of wireless standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. The computing device 600 may include a plurality of communication chips 606. For instance, a first communication chip 606 may be dedicated to shorter range wireless communications such as Wi-Fi and Bluetooth and a second communication chip 606 may be dedicated to longer range wireless communications such as GPS, EDGE, GPRS, CDMA, WiMAX, LTE, Ev-DO, and others.

The processor 604 of the computing device 600 includes an integrated circuit die packaged within the processor 604. In some implementations of the invention, the integrated circuit die of the processor may be packaged on an organic substrate and provide signals for actuating one or more piezoelectric switches in an encryption bank, in accordance with implementations of the invention. The term "processor" may refer to any device or portion of a device that processes electronic data from registers and/or memory to transform that electronic data into other electronic data that may be stored in registers and/or memory.

The communication chip 606 also includes an integrated circuit die packaged within the communication chip 606. In accordance with another implementation of the invention, the integrated circuit die of the communication chip may be packaged on an organic substrate and provide signals for actuating one or more piezoelectric switches in an encryption bank, in accordance with implementations of the invention.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize.

These modifications may be made to the invention in light of the above detailed description. The terms used in the following claims should not be construed to limit the invention to the specific implementations disclosed in the specification and the claims. Rather, the scope of the invention is to be determined entirely by the following claims, which are to be construed in accordance with established doctrines of claim interpretation.

Example 1: a microelectronic package, comprising: a package substrate; a first electrical component; a second electrical component; and an encryption bank formed along a data transmission path between the first electrical component and the second electrical component, wherein the encryption bank comprises a plurality of switches integrated into the package substrate.

Example 2: the microelectronic package of Example 1, wherein the plurality of switches are piezoelectrically driven switches.

Example 3: the microelectronic package of Example 1 or Example 2, wherein each of the plurality of switches comprise: a first electrode; a piezoelectric layer formed on the first electrode; and a second electrode formed on the piezoelectric layer.

Example 4: the microelectronic package of Example 3, wherein the first electrode is formed below the piezoelectric layer and along a first sidewall of the piezoelectric layer, and wherein the second electrode is formed along a second sidewall of the piezoelectric layer that is opposite to the first sidewall.

Example 5: the microelectronic package of Example 3 or Example 4, wherein the second electrode is also formed over a portion of a top surface of the piezoelectric layer.

Example 6: the microelectronic package of Example 3, Example 4, or Example 5, wherein the first electrode and the second electrode extend over a cavity formed in the package substrate and are electrically coupled to anchors on the package substrate.

Example 7: the microelectronic package of Example 6, further comprising: a conductive trace formed along a sidewall of the cavity, wherein one of the first or second electrodes contact the conductive trace when the switch is actuated.

Example 8: the microelectronic package of Example 1, Example 2, Example 3, Example 4, Example 5, Example 6, or Example 7, wherein the first electrode is formed below the piezoelectric layer and the second electrode is formed above the piezoelectric layer.

Example 9: the microelectronic package of Example 1, Example 2, Example 3, Example 4, Example 5, Example 6, Example 7, or Example 8 wherein a bridge trace is formed on the switch below the piezoelectric layer, and wherein the bridge trace is electrically isolated from the first electrode by an insulator material.

Example 10: the microelectronic package of Example 1, Example 2, Example 3, Example 4, Example 5, Example 6, Example 7, Example 8, or Example 9, wherein the bridge trace formed on the piezoelectric switch completes a circuit when the piezoelectric switch is actuated.

Example 11: the microelectronic package of Example 1, Example 2, Example 3, Example 4, Example 5, Example 6, Example 7, Example 8, Example 9, or Example 10, wherein the piezoelectric layer is lead zirconate titanate (PZT), potassium sodium niobate (KNN), zinc oxide (ZnO).

Example 12: the microelectronic package of Example 1, Example 2, Example 3, Example 4, Example 5, Example 6, Example 7, Example 8, Example 9, Example 10, or Example 11, wherein the plurality of switches each include a first portion and a second portion, wherein a cross-sectional area of the first portion is greater than a cross-sectional area of the second portion.

Example 13: the microelectronic package of Example 1, Example 2, Example 3, Example 4, Example 5, Example 6, Example 7, Example 8, Example 9, Example 10, Example 11, or Example 12, wherein the plurality of switches are bi-stable or tri-stable switches.

Example 14: a physiological sensor system, comprising: a package substrate; a plurality of sensors formed on the substrate; a second electrical component; and an encryption bank formed along a data transmission path between the plurality of sensors and the second electrical component, wherein the encryption bank comprises a plurality of portions that each include one or more switches integrated into the package substrate, and wherein each sensor transmits data to the second electrical component along different portions of the encryption bank.

Example 15: the physiological sensor system of Example 14, wherein each of the plurality of sensors, detect inputs that are indicative of a physiological condition.

Example 16: the physiological sensor system of Example 15, wherein the physiological condition is a cardiac event, and wherein the each sensor detects one or more of heart rate, heart arrhythmias, shortness of breath, upper body pain, blood pressure, blood chemistry, body temperature, or sweat.

Example 17: the physiological sensor system of Example 14, Example 15, or Example 16, wherein the second electrical component initiates a response to the physiological condition only when each of the plurality of sensors transmits properly encrypted signals to the second electrical component and each of the sensors report that the physiological condition is occurring or has occurred.

Example 18: the physiological sensor system of Example 14, Example 15, Example 16, or Example 17, wherein each of the plurality of switches comprise: a first electrode; a piezoelectric layer formed on the first electrode; and a second electrode formed on the piezoelectric layer.

Example 19: the physiological sensor system of Example 18, wherein the first electrode is formed below the piezoelectric layer and along a first sidewall of the piezoelectric layer, and wherein the second electrode is formed along a second sidewall of the piezoelectric layer that is opposite to the first sidewall.

Example 20: the physiological sensor system of Example 18 or Example 19, wherein the first electrode is formed below the piezoelectric layer and the second electrode is formed above the formed above the piezoelectric layer.

Example 21: the physiological sensor system of Example 18, Example 19, or Example 20, wherein the piezoelectric layer is lead zirconate titanate (PZT), potassium sodium niobate (KNN), zinc oxide (ZnO).

Example 22: the physiological sensor system of Example 14, Example 15, Example 16, or Example 17, wherein the switches are thermally driven by a resistive heating element.

Example 23: a sensor system, comprising: a package substrate; a plurality of sensors formed on the substrate; a second electrical component; an encryption bank formed along a data transmission path between the plurality of sensors and the second electrical component, wherein the encryption bank comprises a plurality of portions that each include one or more switches integrated into the package substrate, wherein each sensor transmits data to the second electrical component along different portions of the encryption bank, and wherein each of the plurality of switches comprise: a first electrode; a piezoelectric layer formed on the first electrode; and a second electrode formed on the piezoelectric layer; and a random number generator for re-configuring the switches.

Example 24: the sensor system of Example 23, wherein the random number generator re-configures the switches at predetermined times, at random times, or when a threat to the system is detected.

Example 25: the sensor system of Example 23 or Example 24, wherein the random number generator re-configures switches in different portions of the encryption bank at different times.

What is claimed is:

1. A physiological sensor system, comprising:
    a package substrate;
    a plurality of sensors formed on the substrate;
    an electrical component; and
    an encryption bank formed along a data transmission path between the plurality of sensors and the electrical component, wherein the encryption bank comprises a plurality of portions that each include one or more switches integrated into the package substrate, and wherein each sensor transmits data to the electrical component along different portions of the encryption bank.

2. The physiological sensor system of claim 1, wherein each of the plurality of sensors, detect inputs that are indicative of a physiological condition.

3. The physiological sensor system of claim 2, wherein the physiological condition is a cardiac event, and wherein the each sensor detects one or more of heart rate, heart arrhythmias, shortness of breath, upper body pain, blood pressure, blood chemistry, body temperature, or sweat.

4. The physiological sensor system of claim 2, wherein the electrical component initiates a response to the physiological condition only when each of the plurality of sensors transmits properly encrypted signals to the electrical component and each of the sensors report that the physiological condition is occurring or has occurred.

5. The physiological sensor system of claim 1, wherein each of the plurality of switches comprise:
    a first electrode;
    a piezoelectric layer formed on the first electrode; and
    a second electrode formed on the piezoelectric layer.

6. The physiological sensor system of claim 5, wherein the first electrode is formed below the piezoelectric layer and along a first sidewall of the piezoelectric layer, and wherein the second electrode is formed along a second sidewall of the piezoelectric layer that is opposite to the first sidewall.

7. The physiological sensor system of claim 5, wherein the first electrode is formed below the piezoelectric layer and the second electrode is formed above the piezoelectric layer.

8. The physiological sensor system of claim 5, wherein the piezoelectric layer is lead zirconate titanate (PZT), potassium sodium niobate (KNN), zinc oxide (ZnO).

9. The physiological sensor system of claim 1, wherein the switches are thermally driven by a resistive heating element.

10. A sensor system, comprising:
    a package substrate;
    a plurality of sensors formed on the substrate;
    an electrical component;
    an encryption bank formed along a data transmission path between the plurality of sensors and the electrical component, wherein the encryption bank comprises a plurality of portions that each include one or more switches integrated into the package substrate, wherein each sensor transmits data to the electrical component along different portions of the encryption bank, and wherein each of the plurality of switches comprise:
        a first electrode;
        a piezoelectric layer formed on the first electrode; and
        a second electrode formed on the piezoelectric layer; and
    a random number generator for re-configuring the switches.

11. The sensor system of claim 10, wherein the random number generator re-configures the switches at predetermined times, at random times, or when a threat to the system is detected.

12. The sensor system of claim 10, wherein the random number generator re-configures switches in different portions of the encryption bank at different times.

* * * * *